US010130752B2

(12) United States Patent
Abedin et al.

(10) Patent No.: US 10,130,752 B2
(45) Date of Patent: Nov. 20, 2018

(54) PARALLEL PROCESSING OF FLUID COMPONENTS

(71) Applicant: Fenwal, Inc., Lake Zurich, IL (US)

(72) Inventors: Tanima Jahan Abedin, Chicago, IL (US); Kyungyoon Min, Kildeer, IL (US)

(*) Notice: Subject to any disclaimer, the term of this patent is extended or adjusted under 35 U.S.C. 154(b) by 0 days.

(21) Appl. No.: 14/830,896

(22) Filed: Aug. 20, 2015

(65) Prior Publication Data

US 2016/0051744 A1 Feb. 25, 2016

Related U.S. Application Data

(60) Provisional application No. 62/040,216, filed on Aug. 21, 2014.

(51) Int. Cl.
*A61M 1/36* (2006.01)
*A61M 1/26* (2006.01)
(Continued)

(52) U.S. Cl.
CPC ......... *A61M 1/3693* (2013.01); *A01N 1/0278* (2013.01); *A61M 1/262* (2014.02);
(Continued)

(58) Field of Classification Search
CPC ..... A01N 1/0278; A61M 1/262; A61M 1/265; A61M 1/34; A61M 1/342; A61M 1/3437;
(Continued)

(56) References Cited

U.S. PATENT DOCUMENTS

| 5,194,145 A | 3/1993 | Schoendorfer |
| 5,868,696 A | 2/1999 | Giesler et al. |

(Continued)

FOREIGN PATENT DOCUMENTS

| DE | 10216744 A1 | 6/2003 |
| WO | 2012/125457 A1 | 9/2012 |
| WO | 2012/141697 A1 | 10/2012 |

OTHER PUBLICATIONS

Extended European Search Report for European patent application No. 17156441.2, dated May 10, 2017, 15 pages.

*Primary Examiner* — John Kim
(74) *Attorney, Agent, or Firm* — Hanna Yoon; Scott M. Day

(57) ABSTRACT

A kit for blood component processing comprising a fluid circuit into which blood is drawn, wherein the fluid circuit comprises a plurality of pathways; wherein the first pathway is configured to receive blood drawn from a blood source and leads to a separation device, wherein the separation device is configured to separate the blood into components; wherein the second pathway is configured to receive a first component from the separation device and transport at least a portion of the first component to a first processing device, wherein the first processing device may alter the first component to produce a first output; and wherein the third pathway is configured to receive a second component from the separation device and transport at least a portion of the second component to a second processing device, wherein the second processing device may alter the second component to produce a second output.

7 Claims, 11 Drawing Sheets

(51) Int. Cl.
  *A61M 1/34* (2006.01)
  *A61M 1/38* (2006.01)
  *A01N 1/02* (2006.01)

(52) U.S. Cl.
  CPC ........ *A61M 1/3496* (2013.01); *A61M 1/3696* (2014.02); *A61M 1/38* (2013.01); *A61M 1/3679* (2013.01); *A61M 2205/12* (2013.01)

(58) Field of Classification Search
  CPC .. A61M 1/3489; A61M 1/3496; A61M 1/367; A61M 1/3672; A61M 1/3679; A61M 1/3696; A61M 1/3693; A61M 1/38; A61M 2205/12; A61M 2205/123; A61M 2205/125
  See application file for complete search history.

(56) References Cited

U.S. PATENT DOCUMENTS

| | | |
|---|---|---|
| 6,231,536 B1 * | 5/2001 | Lentz .................... A61K 31/00 128/898 |
| 6,569,112 B2 | 5/2003 | Strahilevitz |
| 6,582,386 B2 * | 6/2003 | Min .................... A61M 1/3687 604/6.01 |
| 2002/0128584 A1 | 9/2002 | Westberg |
| 2014/0045671 A1 | 2/2014 | Min et al. |
| 2014/0291248 A1 * | 10/2014 | Foley ................. A61M 1/3679 210/662 |

* cited by examiner

PARALLEL PROCESSING OF FLUID COMPONENTS

CROSS REFERENCE TO RELATED APPLICATIONS

This application claims the benefit of priority to U.S. Provisional Application Ser. No. 62/040,216, filed Aug. 21, 2014, the entire contents being incorporated herein by reference.

FIELD OF THE DISCLOSURE

The present disclosure generally relates to fluid treatment systems and methods. More particularly, the present disclosure relates to systems and methods for separating blood into its constituents and subsequently treating the constituents.

BACKGROUND

A variety of available blood processing systems allows for the collection and processing of particular blood components, rather than whole blood, from donors or patients. In the case of a blood donor, whole blood is drawn from the donor, a desired blood constituent isolated and collected, and the remaining blood components returned to the donor. By removing only particular constituents rather than whole blood, it takes the donor's body a shorter time period to recover to normal blood levels, thereby increasing the frequency with which the donor may donate blood. It is beneficial to increase in this manner the overall supply of blood constituents made available for health care, such as red blood cells (RBCs), leukocytes, plasma, and/or platelets, etc.

In the case of a patient who requires blood therapy, for example due to blood disease, one or more blood components may be in need of treatment. Commonly treated blood components include RBCs, leukocytes, plasma, and/or platelets, etc. In such therapies, whole blood is drawn from the patient, the problematic blood component is separated and undergone a treatment phase, and the remaining blood components and treated blood component are both returned to the patient. The treatment phase of the problematic blood component can include retaining all or a portion of the component and substituting with a suitable replacement fluid, or selectively filtering out the pathogenic compounds from the blood component with or without providing a replacement fluid.

Different disease states may implicate different components of blood. For example, two blood components commonly affected by various disease states include plasma and red blood cells. Examples of diseases that affect plasma and require plasma therapy include immune-mediated diseases, autoimmune diseases, neoplasia, infectious diseases, sepsis, cholesterolemia, organ transplant rejections, microcirculation disorders, and/or ischemic tissue damage, among many others. For a patient with a disease affecting plasma, the treatment phase of the problematic plasma can include retaining all or a portion of the plasma and substituting with a common replacement fluid such as saline, solution containing albumin, and/or donated fresh frozen plasma, or by selectively filtering out through adsorption the pathogenic compound associated with the disease state from the plasma and returning the pathogen-free plasma to the patient. In the case of selective filtration, a processing device, such as an adsorption device or column, can be used to filter out the pathogenic compound for different disease states. For example, low-density lipoprotein (LDL) and/or lipoprotein a (Lp(a)) may selectively be removed from the plasma in hypercholesterolemia cases; pathogenic antibodies removed in autoimmune disease or organ transplant rejection cases; and/or fibrinogen, fibrin, or C-reactive protein removed for microcirculation disorders or ischemic tissue damage cases.

Examples of diseases that affect RBCs and require RBC replacement therapy include sickle cell disease, ABO-incompatible bone marrow transplant cases, multiple types of anemia, malaria, protozoal infections, and/or carbon monoxide poisoning, among other such diseases that affect the red blood cells. For a patient with a disease affecting red blood cells, the treatment phase of the problematic RBCs can be a RBC exchange procedure, which typically involves retaining a substantial portion of the RBCs and substituting with healthy RBCs originating from a donor. The replacement RBCs may join with the patient's non-RBC components (e.g., plasma, leukocytes, platelets, etc.) to re-enter the patient's bloodstream. The treatment phase of the problematic RBCs can also be a RBC depletion procedure, in which greatly elevated numbers of RBCs may be reduced by rapid removal of RBCs. RBC depletion may be appropriate for disease states such as polycythemia vera and iron overload, when it becomes necessary to reduce blood viscosity, RBC volume, and/or iron load. RBC depletion may also be accompanied by fluid substitution in which appropriate replacement fluids such as saline and/or albumin replace removed volume and therefore maintain fluid balance.

The separation phase of blood components from whole blood typically takes place prior to the treatment of the problematic blood component and may be achieved through a spinning membrane or centrifugation, in which whole blood is passed through a centrifuge or membrane after it is withdrawn from the patient. To avoid contamination and possible infection of the patient, the blood is preferably contained within a sealed, sterile fluid flow system during the entire separation process. Typical blood processing systems thus may include a permanent, reusable hardware assembly containing the hardware (drive system, pumps, valve actuators, programmable controller, and the like) that pumps the blood, and a disposable, sealed and sterile fluid circuit that is mounted in cooperation on the hardware. In the case of separation via centrifugation, the hardware assembly includes a centrifuge that may engage and spin a separation chamber of the disposable fluid circuit during a blood separation step. The blood, however, may make actual contact only with the fluid circuit, which assembly may be used only once and then discarded. In the case of separation via a spinning membrane, a disposable single-use spinning membrane may be used in cooperation with the hardware assembly and disposable fluid circuit.

In the case of separation via centrifugation, as the whole blood is spun by the centrifuge, the heavier (greater specific gravity) components, such as red blood cells, move radially outwardly away from the center of rotation toward the outer or "high-G" wall of the separation chamber of the fluid circuit. The lighter (lower specific gravity) components, such as plasma, migrate toward the inner or "low-G" wall of the separation chamber. Various ones of these components can be selectively removed from the whole blood by forming appropriately located channeling seals and outlet ports in the separation chamber of the fluid circuit.

In the case of separation via a spinning membrane, whole blood may be spun within a disposable spinning membrane, rather than within a separation chamber of a fluid circuit. Larger molecules, such as red blood cells, may be retained within one side of the membrane, while the smaller molecules, such as plasma, may escape through the pores of the membrane to the other side of the membrane. Various ones of these components can be selectively removed from the whole blood by forming appropriately located outlet ports in the housing of the membrane column. Various types of columns with different pore sizes may be used, depending on the components to be separated.

SUMMARY

According to an exemplary embodiment, the present disclosure is directed to a disposable kit for blood component processing. The kit may comprise a fluid circuit into which blood is drawn from a blood source, wherein the fluid circuit may comprise a first, second, and third pathway. The first pathway may be configured to receive blood drawn from the blood source and may lead to a separation device, wherein the separation device may be configured to separate the blood into two or more components. The second pathway may be configured to receive a first component from the separation device and may transport at least a portion of the first component to a first processing device, wherein the first processing device may be configured to alter the first component in at least one of volume, constitution, and composition, to produce a first output. The third pathway may be configured to receive a second component from the separation device and transport at least a portion of the second component to a second processing device, wherein the second processing device may be configured to alter the second component in at least one of volume, constitution, and composition, to produce a second output.

According to an exemplary embodiment, the present disclosure is directed to a blood processing method comprising the step of receiving in a fluid circuit blood drawn from a blood source, wherein the fluid circuit may comprise a first, second, and third pathway. The blood processing method may also comprise the step of receiving in the first pathway blood drawn from the blood source, the first pathway leading to a separation device, wherein the separation device may be configured to separate the blood into two or more components. The blood processing method may also comprise the step of receiving in the second pathway a first component from the separation device, the second pathway transporting at least a portion of the first component to a first processing device, wherein the first processing device may be configured to alter the first component in at least one of volume, constitution, and composition, to produce a first output. The blood processing method may also comprise the step of receiving in the third pathway a second component from the separation device, the third pathway transporting at least a portion of the second component to a second processing device, wherein the second processing device may be configured to alter the second component in at least one of volume, constitution, and composition, to produce a second output.

According to an exemplary embodiment, the present disclosure is directed to a disposable kit for blood component processing comprising a fluid circuit into which whole blood may be drawn from a blood source, wherein the fluid circuit may comprise a first, second, third, fourth, fifth, and sixth tubing. The first tubing may be configured to receive blood drawn from the blood source and may lead to a separation device, wherein the separation device may be configured to separate the whole blood into substantially cell-free plasma and cellular components. The second tubing may be configured to receive the substantially cell-free plasma from the separation device and transport at least a portion of the substantially cell-free plasma to a processing device, wherein the processing device may be configured to retain and/or filter all of the substantially cell-free plasma or a portion thereof. The third tubing may be configured to receive the cellular components from the separation device and transport at least a portion of the cellular components to a container in which at least a portion thereof is retained. The fourth tubing may be configured to receive a replacement fluid from a replacement fluid container. The fifth tubing may be configured to receive from the processing device fluid of the substantially cell-free plasma that is not retained by the processing device. The sixth tubing may be configured to receive fluid from the fourth tubing and fifth tubing and transport at least a portion thereof to the blood source.

BRIEF DESCRIPTION OF THE DRAWINGS

Features, aspects, and advantages of the present embodiments will become apparent from the following description, appended claims, and the accompanying exemplary embodiments shown in the drawings, which are briefly described below.

DETAILED DESCRIPTION

There are several aspects of the present subject matter which may be embodied separately or together in the devices and systems described and claimed below. These aspects may be employed alone or in combination with other aspects of the subject matter described herein, and the description of these aspects together is not intended to preclude the use of these aspects separately or the claiming of such aspects separately or in different combinations as set forth in the claims appended hereto.

Some embodiments may allow the simultaneous, parallel, or concurrent performance of differing component therapies for patients with diseases that affect more than one blood component or patients with multiple diseases that cumulatively affect more than one blood component.

Some embodiments may obviate the practice of patients undergoing multiple component therapies (e.g., plasma and RBC therapies) in sequence and independently, with separate disposable fluid circuits and often separate machines.

Some embodiments may shorten the time that it takes to complete an entire treatment and/or decrease the required number of disposable circuit kits.

Some embodiments may decrease the number of patient needle insertions and/or extracorporeal circulations of patient blood.

Simultaneous treatment of two different blood components may be implemented in some embodiments while maintaining the treatment phases of these blood components in separate and/or isolated pathways for the duration of treatment. Keeping these components in separate pathways while undergoing treatment within the same disposable fluid circuit kit may be achieved by some embodiments.

Figure 1:
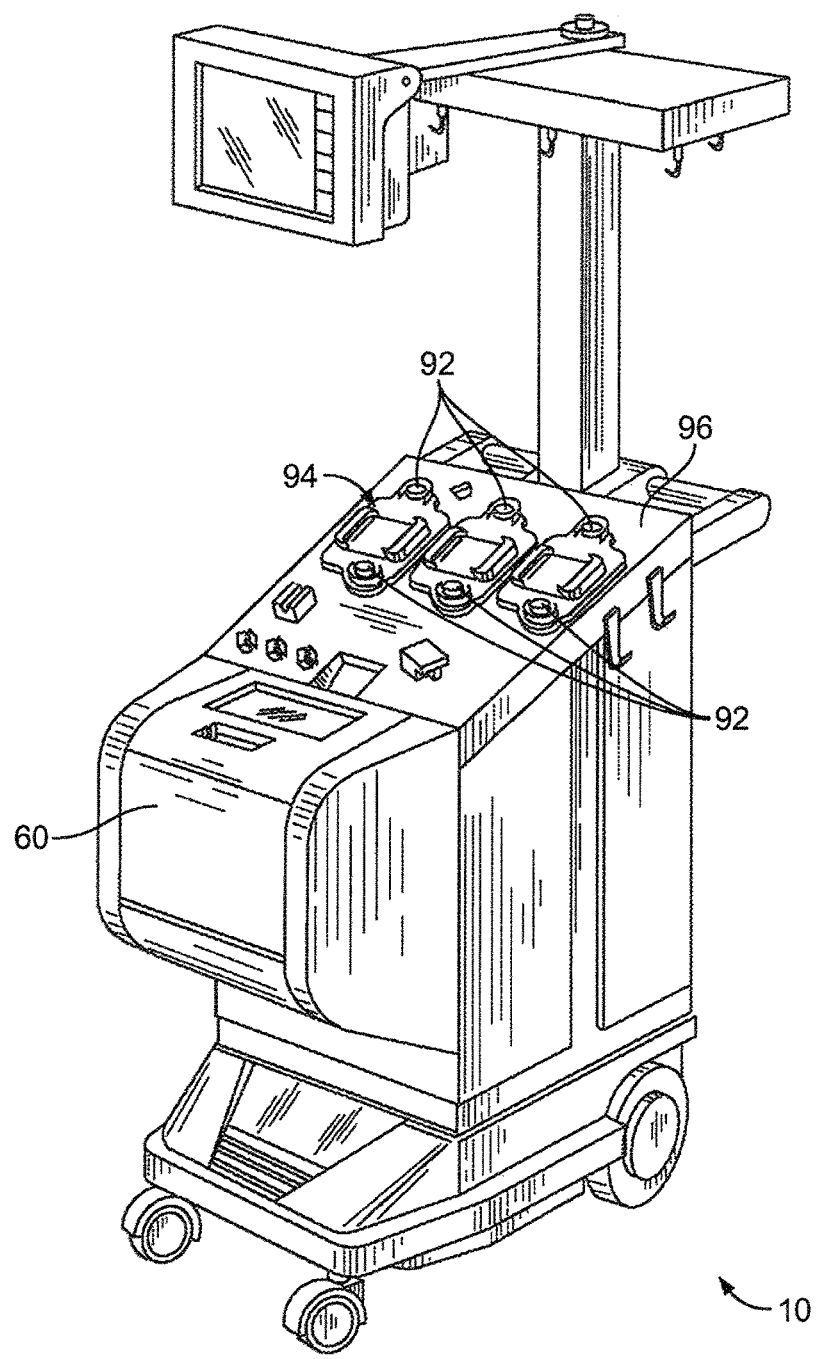
FIG. 1 is a perspective view of a fluid processing system, according to an exemplary embodiment.

FIG. 1 shows an exemplary fluid processing system 10 which may be suitable for use with a centrifuge 52 (FIG. 4) or spinning membrane 35 (FIG. 6A) used in conjunction with a disposable fluid circuit 12. The fluid processing system 10 may have one or more features of an apheresis device, such as a system marketed as the AMICUS® separator by Fenwal, Inc. of Lake Zurich, Ill., as described in greater detail in U.S. Pat. No. 5,868,696, which is hereby incorporated herein by reference in its entirety. The system 10 can be used for processing various fluids, including, but not limited to whole blood, blood components, or other suspensions of biological cellular materials. While improved fluid circuit pathways will be described herein with reference to exemplary system 10, it should be understood that these principles may be employed with other fluid processing systems without departing from the scope of the present disclosure.

Figure 2:
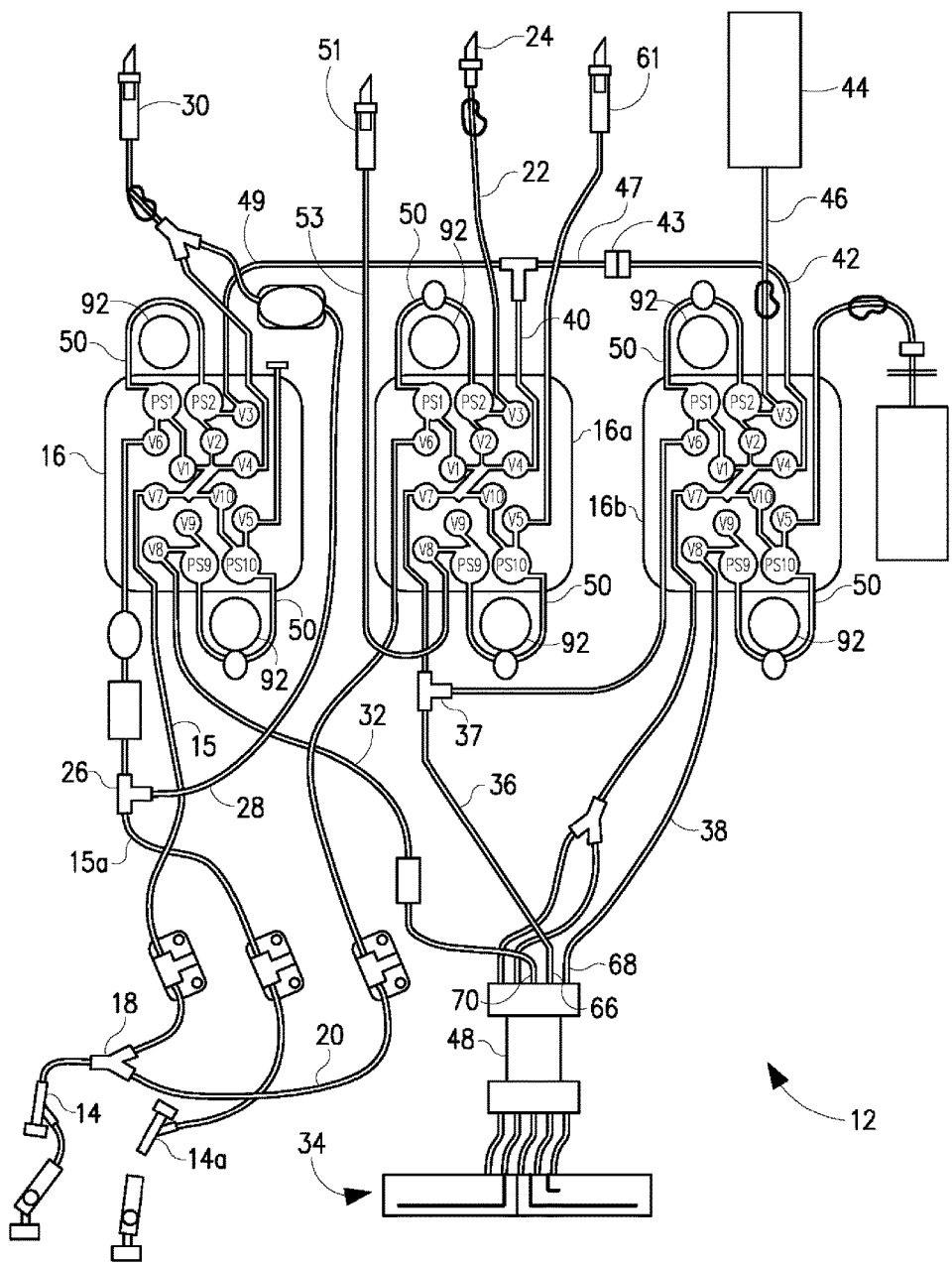
FIG. 2 is a diagrammatic view of a disposable flow circuit that may be used in combination with the fluid processing system of FIG. 1, according to an exemplary embodiment.

The fluid processing system 10 is used in combination with a single-use or disposable flow circuit 12, such as the one illustrated in FIG. 2, to form a separation system. The flow circuit 12 includes a variety of tubing or conduits and a number of other components, only some of which will be described herein in greater detail. The flow circuit 12 of FIG. 2 is specially configured to be used in combination with the fluid processing system 10 of FIG. 1, but it should be understood that the flow circuit may be differently configured if the fluid processing system is differently configured from the embodiment of FIG. 1.

The illustrated flow circuit 12 is a "two needle" system, which includes a pair of blood source access devices 14 and 14a (e.g., phlebotomy needles) for fluidly connecting a blood source (e.g., donor, patient, blood bag, etc.) with the flow circuit 12. The blood source access devices 14 and 14a are connected by tubing to a left cassette 16. A cassette may comprise a case made of plastic or other material configured to facilitate the flow of fluid therethrough. One of the blood source access devices 14 of the flow circuit 12 accesses blood from the blood source and is connected to the left cassette 16 by a y-connector 18. The other leg of the y-connector 18 is connected to tubing 20 which leads to a middle cassette 16a. The tubing 20 is connected, through the middle cassette 16a, to additional tubing 22, which includes a container access device 24 (e.g., a sharpened cannula or spike connector) for accessing the interior of an anticoagulant container (not illustrated). During a blood treatment operation, anticoagulant from the anticoagulant container may be added to the blood from the blood source at the y-connector 18 prior to entering the left cassette 16.

The other blood source access device 14a may be used to deliver or return blood, a blood component, and/or some other replacement fluid to the blood source and is also connected to the left cassette 16 by a y-connector 26. The other leg of the y-connector 26 is connected to tubing 28 connected at its other end to a container access device 30. Although not illustrated, the container access device 30 may be associated with a container having an amount of fluid (e.g., saline) to be used to prime the flow circuit 12 and/or be delivered to the blood source via the blood source access device 14 or 14a.

The left cassette 16 also includes tubing 32 which is connected to a blood separation chamber 34 of the flow circuit 12 (in a centrifugation system) or to a spinning membrane 35 (in a spinning membrane system) for flowing anticoagulated blood thereto. The blood separation chamber 34 or spinning membrane 35 separates the blood into its constituent parts and returns the blood components to other portions of the flow circuit 12. In one embodiment, cellular blood components, such as RBCs, are returned to a right cassette 16b of the flow circuit 12 from the blood separation chamber 34 or spinning membrane 35 via tubing 36 and y-connector 37, while substantially cell-free plasma is returned to the same right cassette 16b of the flow circuit 12 from the blood separation chamber 34 or spinning membrane 35 via tubing 38. The cellular blood components may be pumped through right cassette 16b to container 44, via tubing 46, where they are retained. The substantially cell-free plasma may be pumped through the right cassette 16b and into tubing 42, which may lead to a processing device 43 that selectively filters out designated pathogenic compounds from the plasma and/or may retain a portion of the plasma volume. The processing device 43 may be a plasma reduction container, or any device such as a column described in greater detail in International Publication No. WO 2012/141697 and U.S. Pat. No. 6,569,112, each of which is hereby incorporated by reference herein in its entirety, although any suitable processing device may be used. In the event that the treatment phase of plasma includes plasma reduction, substitution with a common replacement fluid such as saline or solution containing albumin or fresh frozen plasma drawn from container access devices 51 or 61 may be provided as part of the processing.

As used throughout this disclosure, the term processing includes, for example, altering plasma volume, constitution, and/or composition. A volume alteration, for example, may comprise any change in the plasma volume before and after processing. Plasma reduction is one example of a volume alteration, in which the plasma volume before processing may be less than that after processing. Plasma reduction followed by substitution with a replacement fluid is an example of an alteration in constitution and/or composition, in which the plasma subsequent to processing may have a different constitution and/or composition from the plasma prior to processing.

Although in the embodiment presented, both the cellular blood components and the substantially cell-free plasma are returned to the right cassette 16b of the flow circuit 12 via their respective tubings 36 and 38, their pathways within the cassette 16b may remain separate and independent. This may be achieved by a predetermined layout of open and closed valves configured to provide separate and/or independent pathways within cassette 16b. Referring to FIG. 2, while the cellular blood components enter the right cassette 16b via tubing 36 and y-connector 37, valves V1 and V2 of cassette 16b and valve V7 of cassette 16a remain closed while valves V6 and V3 remain open, ensuring that the only pathway available for the cellular blood components is the pathway leading to container 44. At the same time, while the substantially cell-free plasma enters the same right cassette 16b via tubing 38, valves V9, V5, V7, V1, and V2 remain closed while valves V8, V10, and V4 remain open, ensuring that the only pathway available for the plasma is the pathway leading to processing device 43 and/or container 45 via tubing 42. While in this particular embodiment, a specific valve arrangement and cassette 16b are disclosed, a different cassette or cassettes and/or a different valve arrangement may serve a similar purpose.

At a time point in close proximity to the retention of the cellular blood components in container 44, donated healthy red blood cells or an appropriate replacement fluid such as saline or albumin, may be drawn by container access device 51 or container access device 61. In an embodiment in which the healthy RBCs or appropriate replacement fluid are drawn by container access device 51, the donated RBCs or replacement fluid enters the middle cassette 16a via tubing 53 and are led by another predetermined layout of open and closed valves into tubing 40, this time a layout in which valves V7, V1, V2, V9, and V5 are closed, and valves V8, V10, and V4 are open. Meanwhile, treated plasma that has not been retained by the processing device 43 and/or treated plasma that has been filtered through processing device 43 may enter tubing 47. Both the healthy RBCs or replacement fluid from tubing 40 and the treated plasma from tubing 47 then may join pathways as treated whole blood at tubing 49 to jointly enter the left cassette 16. While in this particular embodiment, a specific valve arrangement and cassette 16a are disclosed, a different cassette or cassettes and/or a different valve arrangement may serve a similar purpose.

Inside the left cassette 16, another predetermined layout of open and closed valves may ensure that the pathway of the treated whole blood back to the blood source remains separate and independent from the untreated whole blood that is entering the same left cassette 16 from tubing 15 and blood source access device 14. In one embodiment, valves V1, V2, V4, V5, and V9 remain closed while valves V3, V6, V7, V8, and V10 remain open to provide two separate and independent pathways for outgoing treated and in-coming untreated whole blood. The treated whole blood may leave the left cassette 16 via tubing 15a to blood source access device 14a, where it may re-enter the blood source as healthy whole blood.

Figure 3A:
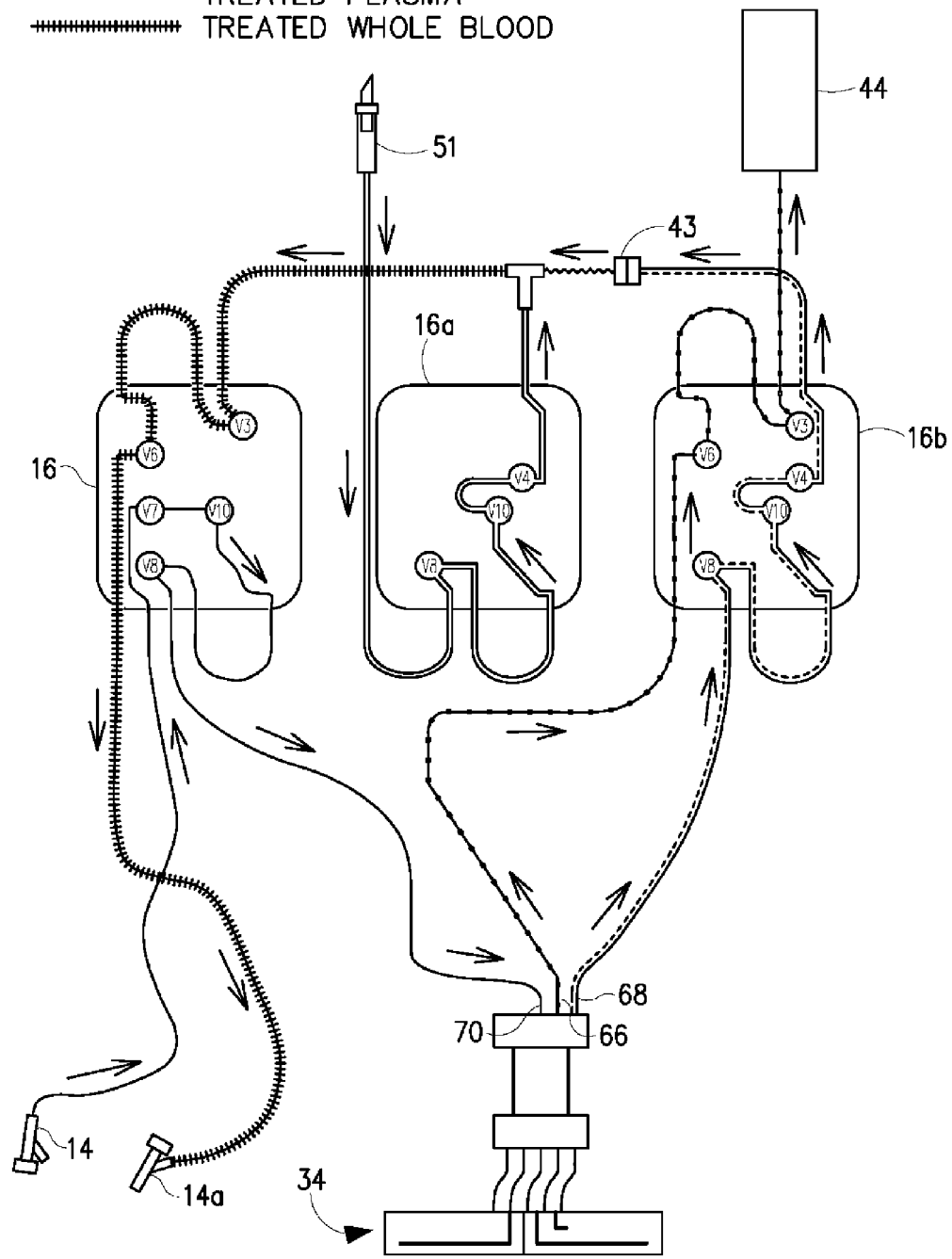
FIG. 3A is an overall schematic diagrammatic view of flow pathways that may be taken by fluid and components within a flow circuit when fluid is separated by a centrifuge, according to an exemplary embodiment.
Figure 3B:
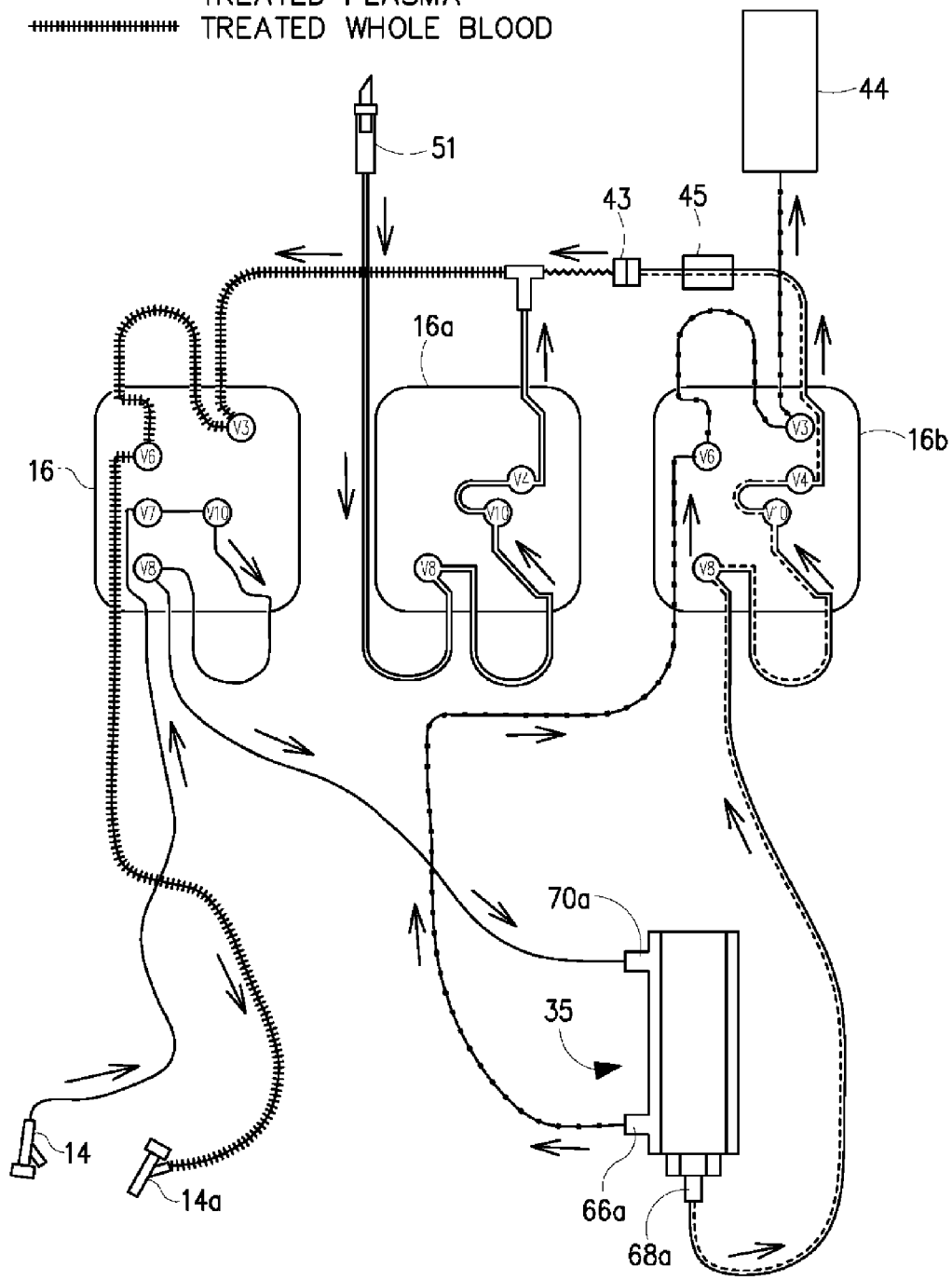
FIG. 3B is an overall schematic diagrammatic view of flow pathways that may be taken by fluid and components within a flow circuit when fluid is separated by a membrane, according to an exemplary embodiment.

FIGS. 3A and 3B are overall schematic diagrams of one embodiment of the flow pathways of untreated whole blood, untreated plasma, untreated cellular blood component, donor RBCs or replacement fluid, treated plasma, and treated whole blood. For simplicity, only open valves are shown. While in this particular embodiment, a specific valve arrangement and cassette 16 are disclosed, it should be contemplated that a different cassette or cassettes and/or a different valve arrangement may serve a similar purpose. Referring to FIGS. 3A and 3B, one of the blood source access devices 14 of the flow circuit 12 accesses blood from the blood source and is connected to the left cassette 16. The other blood source access device 14a may be used to deliver or return blood, a blood component, and/or some other replacement fluid to the blood source and is also connected to the left cassette 16. The left cassette 16 is connected to a blood separation chamber 34 of the flow circuit 12 (in a centrifugation system in FIG. 3A) or to a spinning membrane 35 (in a spinning membrane system in FIG. 3B) for flowing blood thereto. The blood separation chamber 34 or spinning membrane 35 separates the blood into its constituent parts. In one embodiment, cellular blood components, such as RBCs, are returned to a right cassette 16b of the flow circuit 12 from the blood separation chamber 34 or spinning membrane 35, while substantially cell-free plasma is returned to the same right cassette 16b of the flow circuit 12 from the blood separation chamber 34 or spinning membrane 35. The cellular blood components may be pumped through right cassette 16b to container 44, where they may be retained. The substantially cell-free plasma may be pumped through the right cassette 16b, which may lead to a processing device 43 that selectively filters out designated pathogenic compounds from the plasma and/or may retain a portion of the plasma volume. In the event that the treatment phase of plasma includes plasma reduction, substitution with a common replacement fluid such as saline or solution containing albumin or fresh frozen plasma drawn from container access devices 51 may be provided.

Although in the embodiment presented, both the cellular blood components and the substantially cell-free plasma are returned to the right cassette 16b of the flow circuit 12, their pathways within the cassette 16b may remain separate and independent. This may be achieved by a predetermined layout of open and closed valves configured to provide separate and/or independent pathways within cassette 16b.

At a time point in close proximity to the retention of the cellular blood components in container 44, donated healthy red blood cells or an appropriate replacement fluid such as saline or albumin, may be drawn by container access device 51. The donated RBCs or replacement fluid enters the middle cassette 16a. Meanwhile, treated plasma that has not been retained by the processing device 43 and/or treated plasma that has been filtered through processing device 43 may join pathways with the healthy RBCs or replacement fluid. Both the healthy RBCs or replacement fluid and the treated plasma may jointly enter the left cassette 16 as treated whole blood.

Inside the left cassette 16, another predetermined layout of open and closed valves may ensure that the pathway of the treated whole blood back to the blood source remains separate and independent from the untreated whole blood that is entering the same left cassette 16 from tubing 15 and blood source access device 14. The treated whole blood may leave the left cassette 16 to blood source access device 14a, where it may re-enter the blood source as healthy whole blood.

Figure 3C:
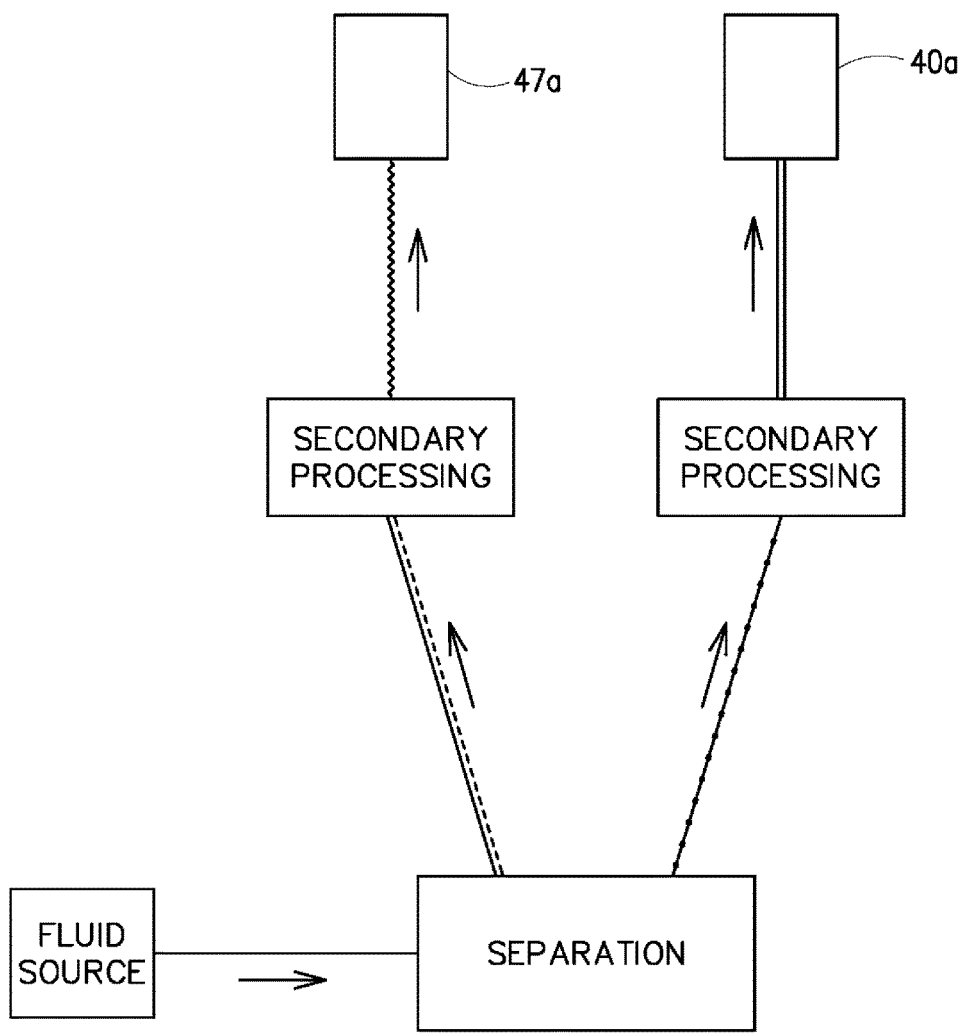
FIG. 3C is an overall schematic diagrammatic view of flow pathways that may be taken by fluid and components within a flow circuit, according to an exemplary embodiment.
Figure 3D:
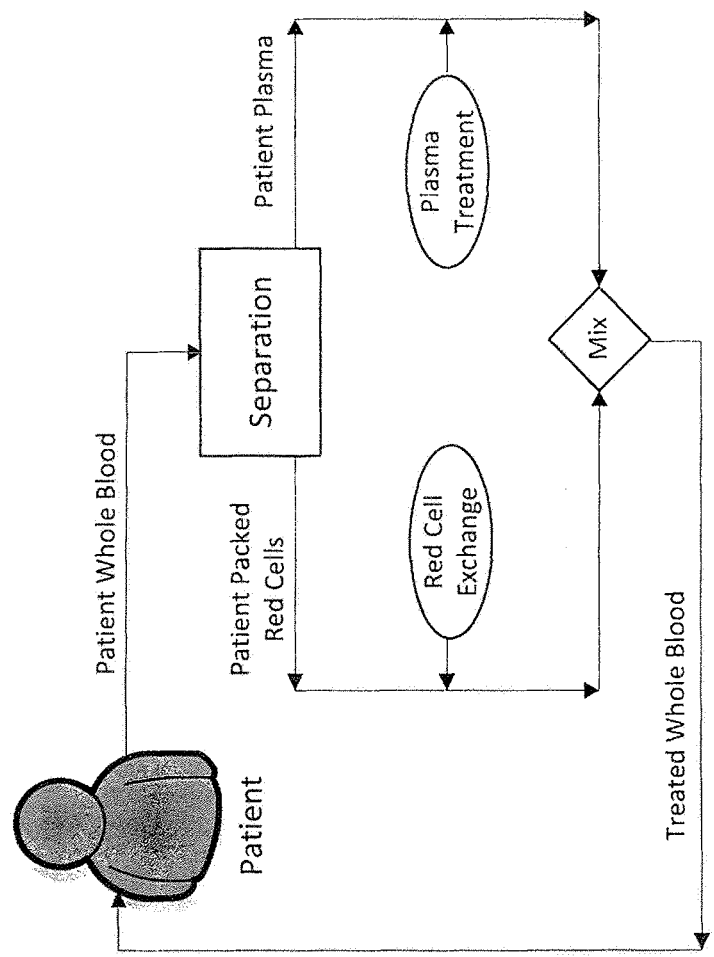
FIG. 3D is an overall schematic diagrammatic view of flow pathways that may be taken by fluid and components through a flow circuit and a patient, according to an exemplary embodiment.

Referring to FIG. 3D, yet another embodiment is shown in which patient whole blood may be separated into components and undergo different therapies. The components may be plasma and red cells, as in the embodiment in FIG. 3D. The components may be separated and treated. In this particular embodiment, RBC exchange takes place for the RBCs in one pathway, and a plasma treatment is executed in another pathway. The treated RBCs and the treated plasma then may join as treated whole blood back to the patient.

As an alternative to an embodiment in which healthy RBCs or replacement fluid and treated plasma join pathways as treated whole blood, treated RBCs and treated plasma may separately be collected in respective containers 40a and 47a, as depicted in FIG. 3C. Such an alternative may be suitable when treated blood components are needed for future use for the donor and/or another patient.

Figure 4:
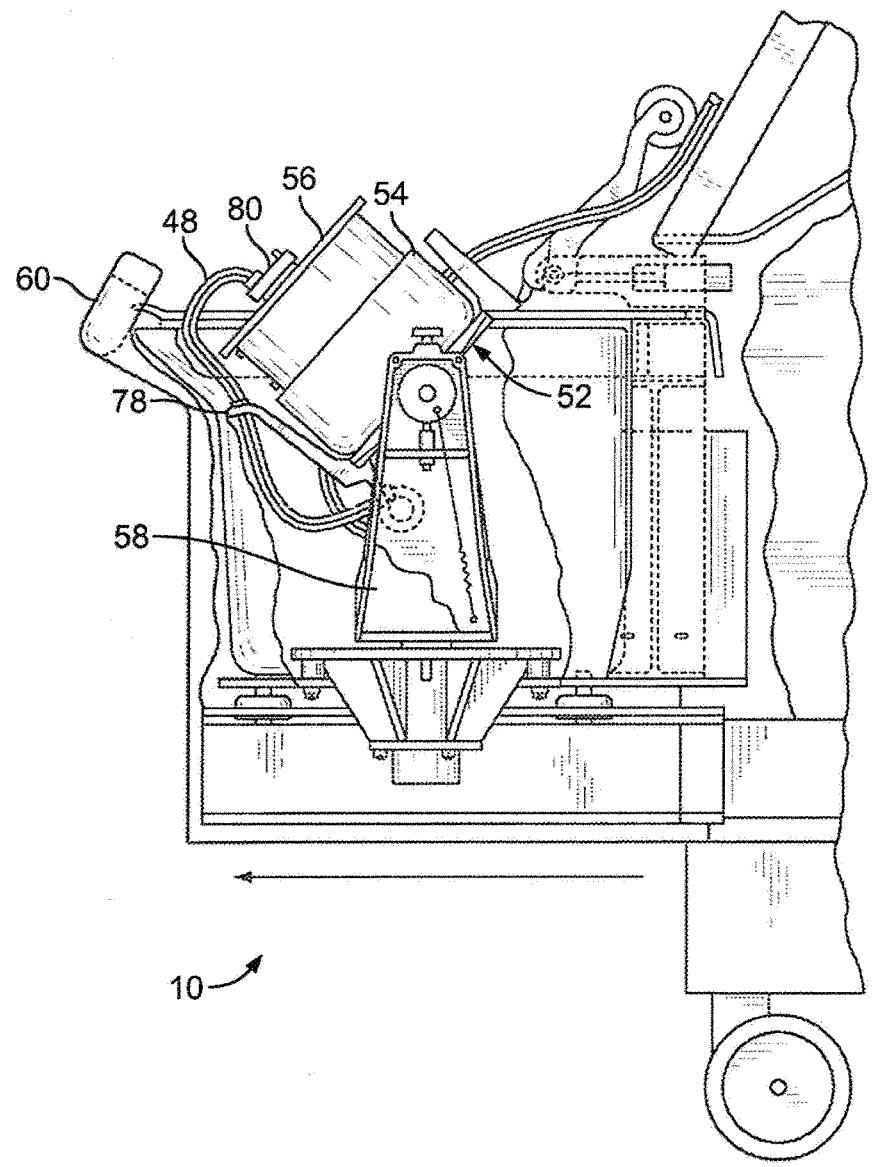
FIG. 4 is a side elevational view, with portions broken away and in section, of the fluid processing system of FIG. 1, with the centrifuge bowl and spool shown in an upright position for receiving a blood separation chamber, according to an exemplary embodiment.

Turning to the fluid processing system of FIG. 4, an embodiment is shown in which the separation method is centrifugation. However, it should be understood that the centrifuge components may be replaced with a spinning membrane and its accompanying hardware or other separation devices. An exemplary spinning membrane and hardware is disclosed in greater detail in PCT Patent Application No. PCT/US2012/28492, which is incorporated herein by reference in its entirety, although any suitable membrane assembly may be used. The fluid processing system 10 of FIG. 4 includes a centrifuge 52 used to centrifugally separate blood components. An exemplary centrifuge is disclosed in U.S. Patent Application Publication No. 2014/0045671, which is incorporated herein by reference in its entirety, although any suitable centrifuge may be used. The centrifuge 52 comprises a bowl 54 and a spool 56, which are pivoted on a yoke 58. The centrifuge 52 is housed within the interior of the fluid processing system 10, so a door 60 is provided to allow access to the centrifuge 52 for loading and unloading the blood separation chamber 34. The door 60 remains closed during operation to protect and enclose the centrifuge 52.

When in a loading or unloading position, the spool 56 can be opened by movement at least partially out of the bowl 54, as FIG. 4 shows. In this position, the operator wraps the flexible blood separation chamber 34 about the spool 56 (see FIG. 5). Closure of the spool 56 and bowl 54 encloses the chamber 34 for processing.

Figure 6:
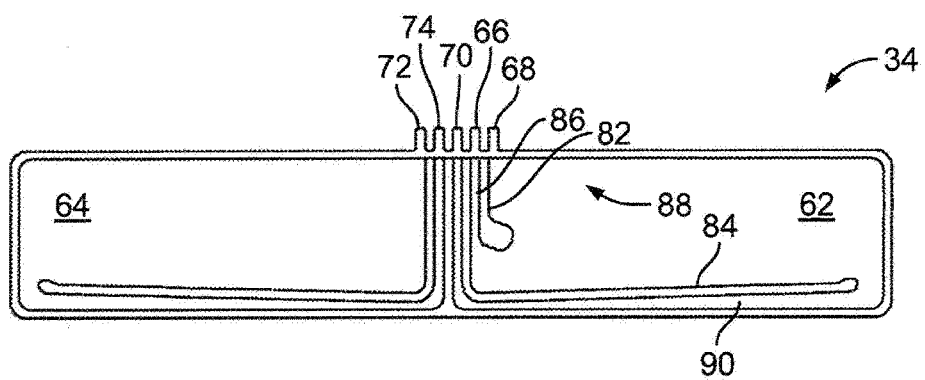
FIG. 6 is a plan view of the blood separation chamber of FIG. 5, out of association with the spool, according to an exemplary embodiment.
Figure 6A:
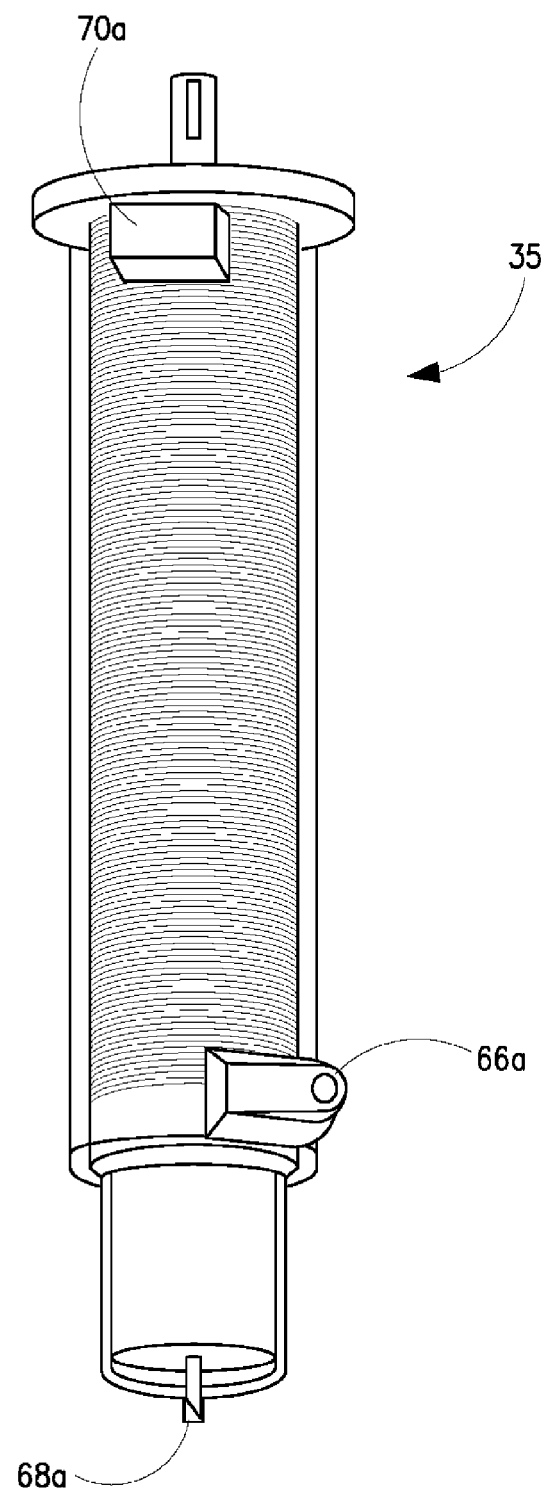
FIG. 6A is a perspective view of a spinning membrane that may be used as the separation device in lieu of a centrifuge, according to an exemplary embodiment.

FIG. 6 shows a representative embodiment of a blood separation chamber 34 which may be used in connection with a suitable centrifuge. The chamber 34 shown in FIG. 6 allows for either single- or multi-stage processing. When used for multi-stage processing, a first stage 62 separates whole blood into first and second components. Depending on the nature of the separation procedure, one of the components may be transferred into a second stage 64 for further processing, although the present disclosure focuses on the first stage 62.

Figure 5:
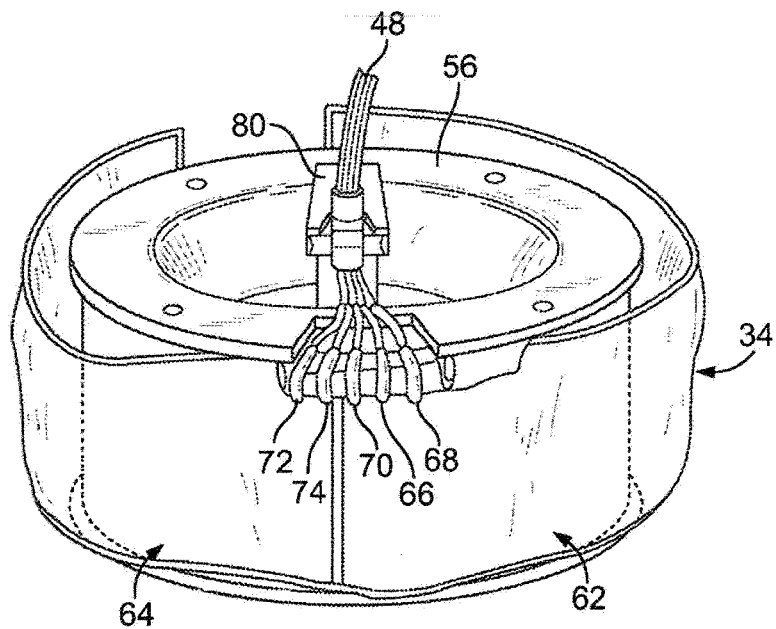
FIG. 5 is a top perspective view of the spool of the fluid processing system of FIG. 4 in its upright position and carrying the blood separation chamber of the flow circuit of FIG. 2, according to an exemplary embodiment.

As FIGS. 5 and 6 show, there may be three ports 66, 68, and 70 associated with the first stage 62. Depending on the particular blood processing procedure, the ports may have different functionality but, in one embodiment, the port identified at 70 may be used for conveying blood from a blood source into the first stage 62 via tubing 32 of the flow circuit 12. The other two ports 66 and 68 may serve as outlet ports for passing separated blood components from the first stage 62 to the flow circuit 12 via tubing 36 and 38, respectively. More particularly, the first outlet port 68 may convey a low density blood component from the first stage 62, while the second outlet port 66 may convey a high density blood component from the first stage 62.

As best shown in FIG. 5, a tubing umbilicus 48 of the flow circuit 12 is attached to the ports 66, 68, 70, 72, and 74. The umbilicus 48 interconnects the first and second stages 62 and 64 with each other and with the components of the flow circuit 12 positioned outside of the centrifuge 52.

As FIG. 6 shows, a first interior seal 82 is located between the low density or plasma outlet port 68 and the high density or red cell outlet port 66. A second interior seal 84 is located between the high density outlet port 66 and the blood inlet port 70. The interior seals 82 and 84 form a fluid path or passage 86 (an outlet for high density blood components) and a low density collection path or region 88. The second seal 84 also forms a fluid passage 90, which in this embodiment allows for a blood inlet.

Blood entering the blood separation chamber 34 is pumped thereinto by one or more pumps 92 of the fluid processing system 10 (FIGS. 1 and 2) acting upon one or more of the tubing loops 50 extending from the cassettes 16-16b of the flow circuit 12 (FIG. 2). An exemplary cassette 16 is illustrated in greater detail in FIGS. 7 and 8, while the pumps 92 and associated cassette holder 94 are shown in greater detail in FIG. 9.

Before beginning a given blood processing and collection procedure, the operator may load various components of the flow circuit 12 onto the sloped front panel 96 and centrifuge 52 of the centrifuge system 10. The blood separation chamber 34 and the umbilicus 48 of the flow circuit 12 are loaded into the centrifuge 52, with a portion of the umbilicus 48 extending outside of the interior of the fluid processing system 10, as shown in FIG. 4. The sloped front panel 96 of the fluid processing system 10 includes at least one cassette holder 94 (three in the illustrated embodiment), each of which is configured to receive and grip an associated cassette 16-16b of the flow circuit 12.

Figure 7:
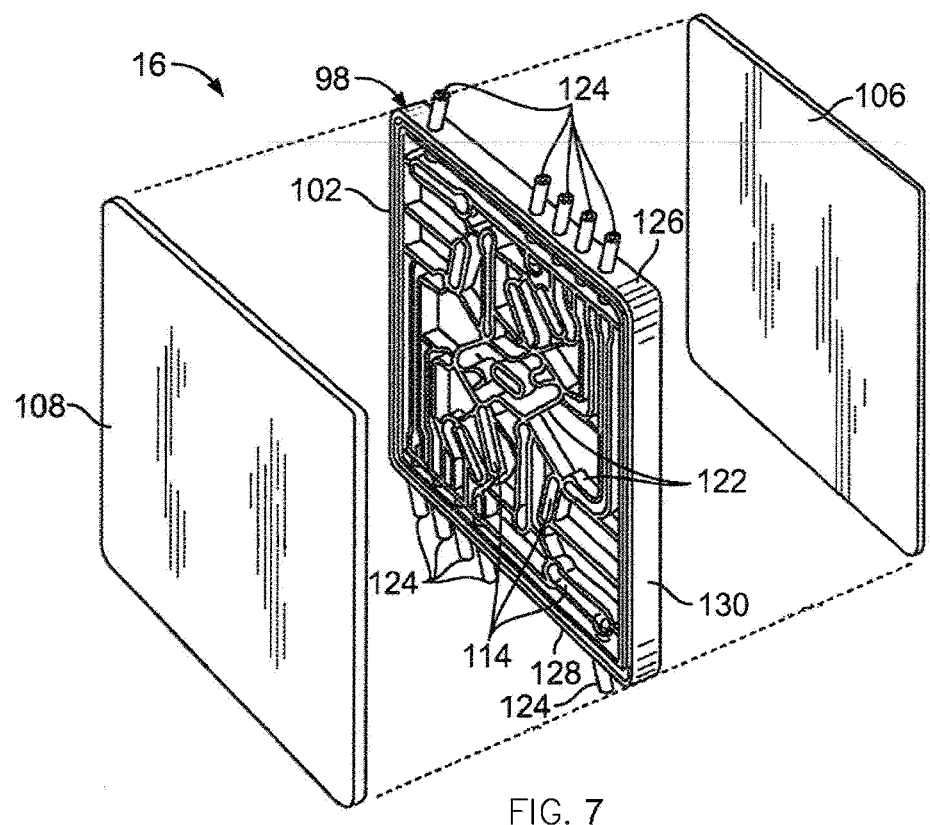
FIG. 7 is an exploded perspective view of a fluid processing cassette of the flow circuit of FIG. 2, according to an exemplary embodiment.
Figure 8:
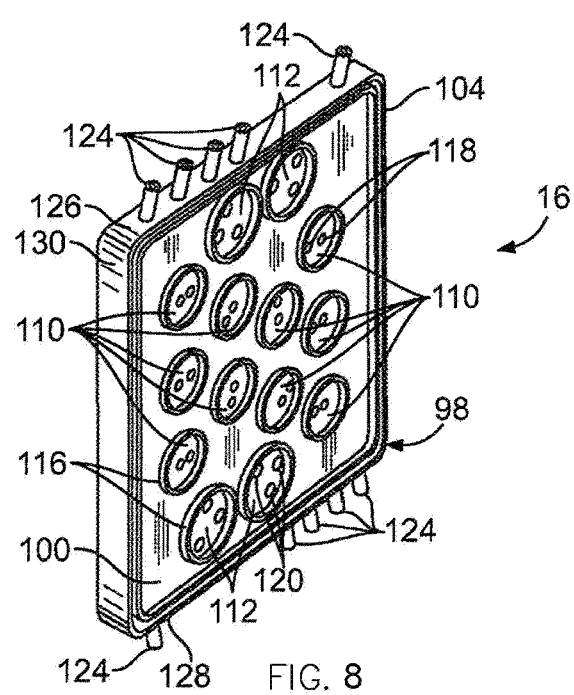
FIG. 8 is a perspective view of an underside of the fluid processing cassette of FIG. 7, according to an exemplary embodiment.

Each cassette 16-16b, one of which is shown in FIGS. 7 and 8, may include an injection molded body 98 that is compartmentalized by an interior wall 100 (FIG. 8) to present or form a topside 102 (FIG. 7) and an underside 104 (FIG. 8). For the purposes of description, the topside 102 is the side of the cassette 16 that, in use, faces away from the centrifuge system 10, while the underside 104 faces towards the centrifuge system 10. A flexible diaphragm 106 may overlie and peripherally seal the underside 104 of the cassette 16. A generally rigid upper panel 108 may overlie the topside 102 of the cassette 16 and may be sealed peripherally and to the raised channel-defining walls in the cassette 16.

In one embodiment, the cassette 16, the interior wall 100, and the upper panel 108 may be made of a rigid medical grade plastic material, while the diaphragm 106 may be made of a flexible sheet of medical grade plastic. The upper panel 108 and the diaphragm 106 may be sealed about their peripheries to the peripheral edges of the top- and undersides 102, 104 of the cassette 16, respectively.

As shown in FIGS. 7 and 8, the top- and undersides 102, 104 of the cassette 16 contain preformed cavities. On the underside 104 of the cassette 16 (FIG. 8), the cavities form an array of valve stations 110 and an array of pressure sensing stations 112. On the topside 102 of the cassette 16 (FIG. 7), the cavities form an array of channels or paths 114 for conveying liquids. The valve stations 110 communicate with the liquid paths 114 through the interior wall 100 to interconnect them in a predetermined manner. The sensing stations 112 also communicate with the liquid paths 114 through the interior wall 100 to sense pressures in selected regions. The number and arrangement of the liquid paths 114, the valve stations 110, and the sensing stations 112 can vary but, in the illustrated embodiment, the cassette 16 may provide nineteen liquid paths 114, ten valve stations 110, and four sensing stations 112.

The valve and sensing stations 110, 112 resemble shallow wells open on the cassette underside 104 (FIG. 8). Upstanding edges 116 rise from the interior wall 100 and peripherally surround the valve and sensing stations 110, 112. The valve stations 110 are closed by the interior wall 100 on the topside 102 of the cassette 16, except that each valve station 110 includes a pair of through holes or ports 118 in the interior wall 100. The ports 118 each open into selected different liquid paths 114 on the topside 102 of the cassette 16.

The sensing stations 112 are likewise closed by the interior wall 100 on the topside 102 of the cassette 16, except that each sensing station 112 includes three through holes or ports 120 in the interior wall 100 (FIG. 8). The ports 120 open into selected liquid paths 114 on the topside 102 of the cassette 16. These ports 120 channel liquid flow among the selected liquid paths 114 through the associated sensing station 112.

In one embodiment, the flexible diaphragm 106 overlying the underside 104 of the cassette 16 is sealed by ultrasonic welding to the upstanding peripheral edges 116 of the valve and sensing stations 110, 112. This isolates the valve stations 110 and sensing stations 112 from each other and the rest of the system. In an alternative embodiment, the flexible diaphragm 106 can be seated against the upstanding edges 116 by an external positive force applied by the cassette holder 94 against the diaphragm 106. The positive force, like the ultrasonic weld, peripherally seals the valve and sensing stations 110, 112.

The localized application of additional positive force (referred to herein as a "closing force") upon the intermediate region of the diaphragm 106 overlying a valve station 110 serves to flex the diaphragm 106 into the valve station 110. Such closing force is provided by the cassette holder 94. The diaphragm 106 seats against one of the ports 118 to seal the port 118, which closes the valve station 110 to liquid flow. Upon removal of the closing force, fluid pressure within the valve station 110, the application of a vacuum to the outer surface of the diaphragm 106, and/or the plastic memory of the diaphragm 106 itself unseats the diaphragm 106 from the port 118, opening the valve station 110 to liquid flow.

Upstanding channel sides or edges 122 rise from the interior wall 100 to peripherally surround and define the liquid paths 114, which are open on the topside 102 of the cassette 16. The liquid paths 114 are closed by the interior wall 100 on the underside 104 of the cassette 16, except for the ports 118, 120 of the valve and sensing stations 110, 112 (FIG. 8). The rigid panel 108 overlying the topside 102 of the cassette 16 is sealed by ultrasonic welding to the upstanding peripheral edges 122, sealing the liquid paths 114 from each other and the rest of the system.

In the illustrated embodiment, ten pre-molded tube connectors 124 extend out along opposite side edges 126, 128 of each cassette 16. The tube connectors 124 are arranged five on one side edge 126 and five on the other side edge 128. The other side edges 130 of the cassette 16, as illustrated, are free of tube connectors. The tube connectors 124 are associated with external tubing (FIG. 2) to associate the cassettes 16 with the remainder of the flow circuit 12, as described above.

The tube connectors 124 communicate with various interior liquid paths 114, which constitute the liquid paths of the cassette 16 through which a fluid enters or exits the cassette 16. The remaining interior liquid paths 114 of the cassette 16 constitute branch paths that link the liquid paths 114 associated with the tube connectors 124 to each other through the valve stations 110 and sensing stations 112.

Figure 9:
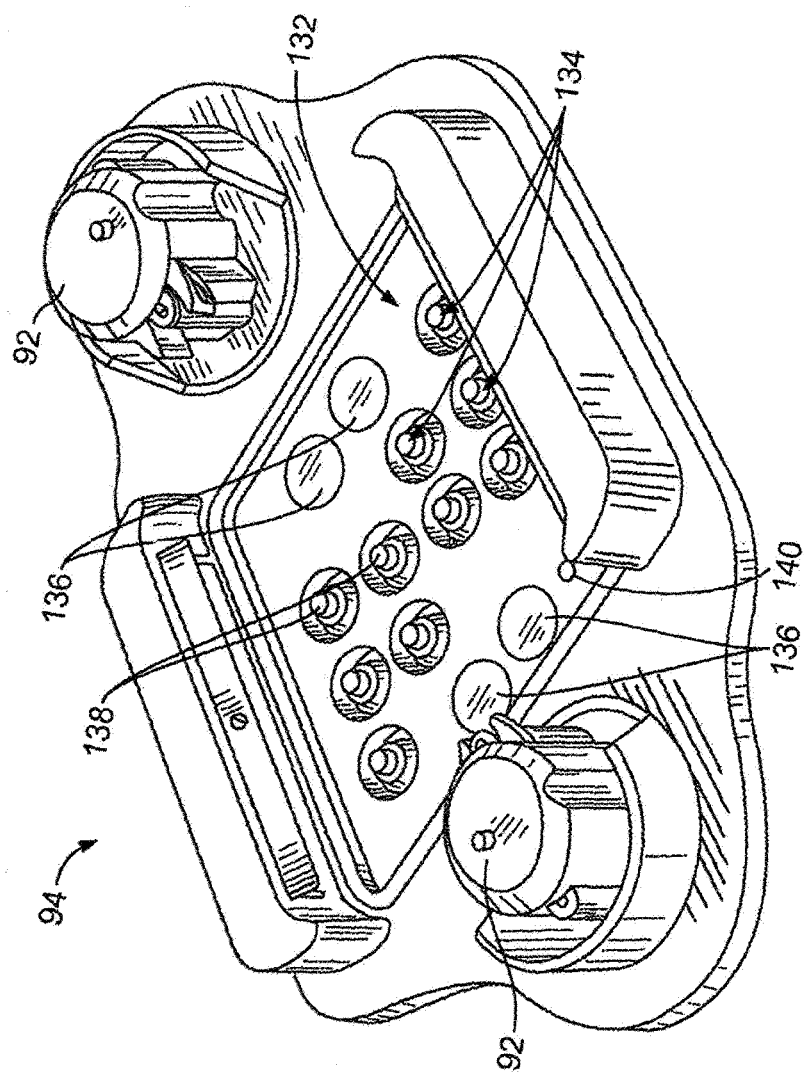
FIG. 9 is a perspective view of a cassette holder of the fluid processing system of FIG. 1, according to an exemplary embodiment.

Turning now to the cassette holders 94 (FIG. 9), each may receive and grip one of the cassettes 16-16b along the two opposed sides edges 130 in the desired operating position. The cassette holder 94 includes a pair of peristaltic pump stations 92. When the cassette 16 is gripped by the cassette holder 94, tubing loops 50 extending from the cassette 16 (FIG. 2) make operative engagement with the pump stations 92 (FIG. 9). The pump stations 92 are operated to cause fluid flow through the cassette 16.

The flexible diaphragm 106 covering the underside 104 of the cassette 16 is urged into intimate contact with a valve and sensor array or assembly 132 by the cassette holder 94. The valve assembly 132 acts in concert with the valve stations 110 and sensing stations 112 of the cassette 16. The valve assembly 132 illustrated in FIG. 9 includes ten valve actuators 134 and four pressure sensing transducers 136. The valve actuators 134 and the pressure sensing transducers 136 are mutually arranged in the same layout as the valve stations 110 and sensing stations 112 on the underside 104 of the cassette 16. When the cassette 16 is gripped by the cassette holder 94, the valve actuators 134 align with the cassette valve stations 110. At the same time, the pressure sensing transducers 136 mutually align with the cassette sensing stations 112.

In one embodiment, each valve actuator 134 includes an electrically actuated solenoid pin or piston 138. Each piston 138 is independently movable between an extended position and a retracted position. When in its extended position, the piston 138 presses against the region of the diaphragm 106 that overlies the associated valve station 110. In this position, the piston 138 flexes the diaphragm 106 into the associated valve station 110, thereby sealing the associated valve port 118. This closes the valve station 110 to liquid flow. When in its retracted position, the piston 138 does not apply force against the diaphragm 106. As before described, the plastic memory of the diaphragm 106 may be such that the removal of force is sufficient for the diaphragm to unseat from the valve port 118, thereby opening the valve station 110 to liquid flow. Alternatively, a vacuum may be applied to the diaphragm 106, for example by the vacuum port 140 illustrated in FIG. 9, to actively unseat the diaphragm 106 from the valve port 118.

The pressure sensing transducers 136 sense liquid pressures in the sensing stations 112 of the cassette 16. The sensed pressures are transmitted to a controller of the centrifuge system 10 as part of its overall system monitoring function. If provided, the vacuum port 140 of the cassette holder 94 may provide suction to the diaphragm 106 of the cassette 16, drawing it into close contact with the transducers 136 for more accurate pressure readings.

The embodiments disclosed herein are for the purpose of providing a description of the present subject matter, and it is understood that the subject matter may be embodied in various other forms and combinations not shown in detail. While described with reference to a blood component processing device, the subject matter presented herein may be applied to other fluid processing devices and medical devices. In some embodiments, the teachings herein could be used on any medical device that involves the parallel processing or treatment of fluid components. Therefore, specific embodiments and features disclosed herein are not to be interpreted as limiting the subject matter as defined in the accompanying claims.

The invention claimed is:

1. A blood processing method using a single fluid circuit and a single medical device comprising the steps of:

receiving in a fluid circuit of a single medical device, blood drawn from a blood source, wherein the fluid circuit comprises a plurality of pathways;

receiving in a first pathway of the single medical device, blood drawn from the blood source, the first pathway leading to a separation device of the single medical device;

separating via the separation device the blood into plasma and red blood cells two or more components;

receiving in a second pathway of the single medical device, the plasma a first component from the separation device;

transporting via the second pathway at least a portion of the plasma first component to a first processing device;

treating via the first processing device the plasma first component o produce a first output treated plasma into a third pathway;

receiving in a fourth pathway of the single medical device, the red blood cells a second component from the separation device;

transporting via the fourth pathway the red blood cells at least a portion of the second component to a container second processing device;

receiving in a fifth pathway donated red blood cells;

treating via the second processing device the second component in parallel with treatment of the first component by the first processing device, to produce a second output into a fifth pathway;

converging the treated plasma first output from the third pathway and the donated red blood cells second output from the fifth pathway at a junction of the third and fifth pathways; and receiving in a sixth pathway of the single medical device, the converged plasma and donated red blood cells first and second outputs from the junction;

wherein the second pathway and the fourth pathway transporting the plasma and the red blood cells, respectively, extend from a first cassette of the single medical device, wherein the fifth pathway extends from a second cassette of the single medical device and wherein the first pathway in and the sixth pathway extend from a third cassette of the single medical device.

2. The blood processing method of claim 1, wherein at least one of the first and second processing device devices is a column.

3. The blood processing method of claim 1, wherein at least one of the first processing device and second processing devices is configured to alter the plasma respective component by displacing at least a portion of the plasma respective component with albumin.

4. The blood processing method of claim 1, further comprising maintaining two or more pathways substantially isolated from each other via a layout of open and closed valves.

5. The blood processing method of claim 1, further comprising maintaining two or more pathways isolated from each other by way of open and closed valves.

6. The blood processing method of claim 1, further comprising altering via the first processing device the plasma first component in constitution to produce the treated plasma first output.

7. The blood processing method of claim 1 further comprising controlling flow through each of the first cassette, the second cassette and the third cassette with valves provided in the first cassette, the second cassette and the third cassette.

* * * * *